United States Patent [19]

Heindel et al.

[11] Patent Number: 4,950,770

[45] Date of Patent: Aug. 21, 1990

[54] PSORALENS AMINOMETHYLATION

[75] Inventors: Ned D. Heindel, Easton; Mridula D. Choudhuri, Whitehall, both of Pa.

[73] Assignee: Elder Pharmaceuticals, Inc., Costa Mesa, Calif.

[21] Appl. No.: 220,874

[22] Filed: Jul. 14, 1988

Related U.S. Application Data

[63] Continuation of Ser. No. 65,077, Jun. 16, 1987, abandoned, which is a continuation of Ser. No. 706,831, Feb. 28, 1985, abandoned.

[51] Int. Cl.$^5$ ............................................ C07D 493/04
[52] U.S. Cl. ..................................................... 549/282
[58] Field of Search ........................................ 549/282

[56] References Cited

U.S. PATENT DOCUMENTS

| | | | |
|---|---|---|---|
| 4,124,598 | 11/1978 | Hearst et al. | 548/463 |
| 4,294,822 | 10/1981 | Kaufman | 549/282 |
| 4,465,842 | 8/1984 | Desbois et al. | 546/219 |

Primary Examiner—Jane T. Fan
Attorney, Agent, or Firm—Lyon & Lyon

[57] ABSTRACT

A direct, acid-catalyzed substitution reaction incorporates an N-phthalimidomethyl group on the 4' or 5' carbon of a psoralen in yields of 60–80% via the condensation of an N-hydroxymethylamide or phthalimide (e.g. N-hydroxymethylphthalimide) and an appropriately substituted psoralen. The phthalimide moiety is cleaved from the psoralen ring by treatment with hydrazine to give 60 to 70% yields of the aminomethylpsoralens.

10 Claims, No Drawings

PSORALENS AMINOMETHYLATION

This is a continuation of co-pending application Ser. No. 07/065,077, filed on June 16, 1987, now abandoned and which is a continuation of application Ser. No. 06/706,831, filed 2/28/85 now abandoned.

RELATED U.S. PATENTS

This application is related to U.S. Pat. No. 4,294,822, issued Oct. 13, 1981, the disclosure of which is incorporated herein by reference.

BACKGROUND OF INVENTION

1. Field of the Invention

The field of the present invention is psoralens, aminomethylation of psoralens and aminomethylpsoralen products.

2. Prior Art

Aminomethyl groups have been introduced into psoralens by condensation of the psoralen with an alpha-halomethyl ether, displacement of the halogen from the halomethyl group with potassium phthalimide and hydrolysis of the resulting N-phthalimidomethyl with hydrazine to generate the aminomethylpsoralens. This three-step process has been described in S. T. Isaacs, C. J. Shen, J. E. Hearst, and H. Rapoport, *Biochem.*, Vol. 16, 1058 (1977), K. Kaufman, et al., *J. Heterocyclic Chem.*, Vol. 19, 1051 (1982), U.S. Pat. Nos. 4,124,598 and 4,294,822. All of these disclosed procedures employ volatile, hydrolytically unstable, carcinogenic haloalkyl ethers whose cancer-causing propensities have been noted (Federal Register, 39, 3756 (1974)). All of these procedures require three synthetic steps with attendant losses of time and efficiency of operation; oveall conversions from psoralen to aminomethylpsoralen of 30–50% have been reported. The conventional three-step procedure is shown below:

ring system (numbering and basic structure shown below):

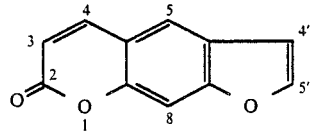

Psoralens or furocoumarins are photochemotherapeutics of broad utility in the treatment of dermatological conditions. Those bearing the aminomethyl group constitute a special subclass of hydrophilic psoralens of significant dermal photosensitizing activity as disclosed in U.S. Pat. No. 4,294,822.

In contrast with prior art procedures, the present process for preparation of aminomethylpsoralens utilizes no volatile reactants and no carcinogenic haloalkylethers. Moreover, this process effects in two steps, with higher overall conversion efficiencies, a process previously described as requiring three distinct chemical operations. The advantages of the present technique result in an improvement in product purity and enhanced efficiency, yield and selectivity of product formation.

The process can be applied to psoralens of the following general structure:

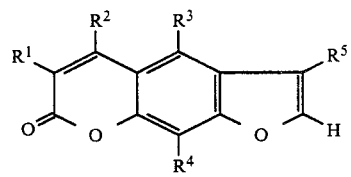

SUMMARY OF THE INVENTION

The present invention is directed to a new synthetic method for introduction of the aminomethyl moiety (i.e., —CH$_2$NH$_2$) onto the psoralen or furocoumarin

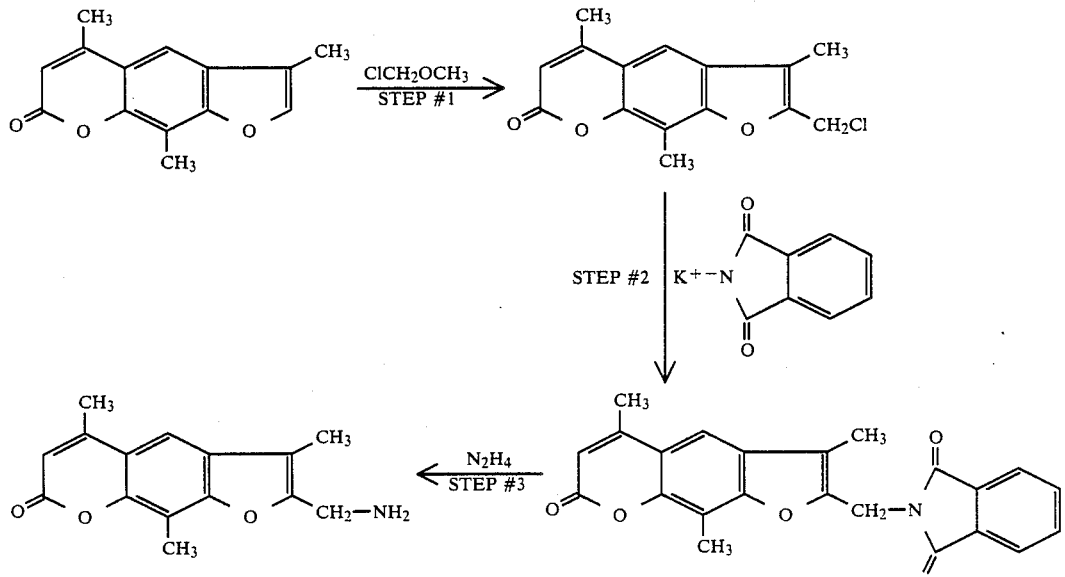

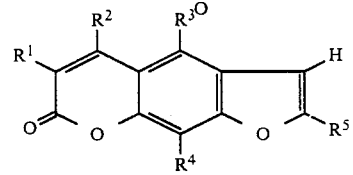

where $R^1$, $R^2$, $R^3$, $R^4$, and $R^5$ are either hydrogen or lower alkyl (methyl, ethyl, propyl, butyl)

with hydrogen, methyl and other lower alkyl substituents on the 3, 4, 5, 8, 4' and 5' positions of the psoralen ring with the requirement that either the 4' or 5' position must bear a hydrogen in order to effect this transformation according to the process disclosed herein. This process, therefore, leads to compounds of the general formula:

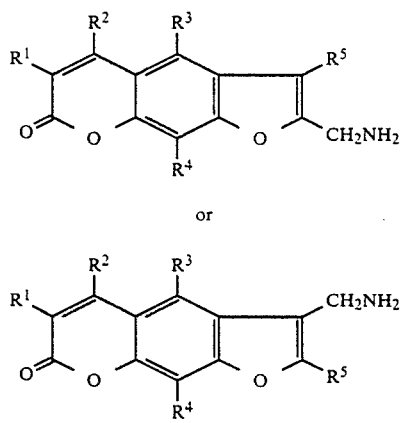

or wherein $R^1$, $R^2$, $R^3$ and $R^4$ are hydrogen, methyl or lower alkyl groups and $R^5$ is methyl or lower alkyl. Hydrochloride salts of these types of compounds are also prepared by this process.

Accordingly, it is an object of the present invention to provide an improved method for introducing the aminomethyl moiety onto psoralen or furocoumarin ring structures.

DETAILED DESCRIPTION OF THE INVENTION

The following Preparations and Examples are given by way of illustration only and are not intended or construed as limiting.

Appropriately substituted starting psoralens (viz, 4,5',8-trimethylpsoralen, 4,4',8-trimethylpsoralen, 4',8-dimethyl-4-propylpsoralen, 4'-ethyl-4,8-dimethylpsoralen, 4,4'-dimethyl-8-ethylpsoralen, 4,5'-dimethylpsoralen, 5',8-dimethylpsoralen, and other hydrogen-, methyl-, ethyl-, and propyl-substituted psoralens) can be prepared by known procedures (J. K. MacLeod and B. R. Worth, *Tetrahedron Lett.*, 237–240 (1972); K. D. Kaufman, *J. Org. Chem.*, 26, 117 (1961); K. D. Kaufman, F. J. Gaiser, T. D. Leth, and L. R. Worden, *J. Org. Chem.*, 26, 2443 (1961); K. D. Kaufman, W. R. Russey, and L. R. Worden, *J. Org. Chem.*, 27, 875 (1962); U.S. Pat. Nos. 4,216,154; and 4,235,781) or by variants of the methods described in these procedures.

Step I of the reaction is effected by bringing a mixture of the psoralen and N-hydroxymethylphthalimide (suspended or dissolved in an anhydrous polar solvent such as chloroform, methylene chloride, acetic acid or formic acid) into contact with a strong protonic or Lewis acid or a mixture of such acids (viz, trifluoracetic acid, methanesulfonic acid, trifluoromethanesulfonic acid, boron trifluoride etherate, fuming sulfuric acid).

STEP I

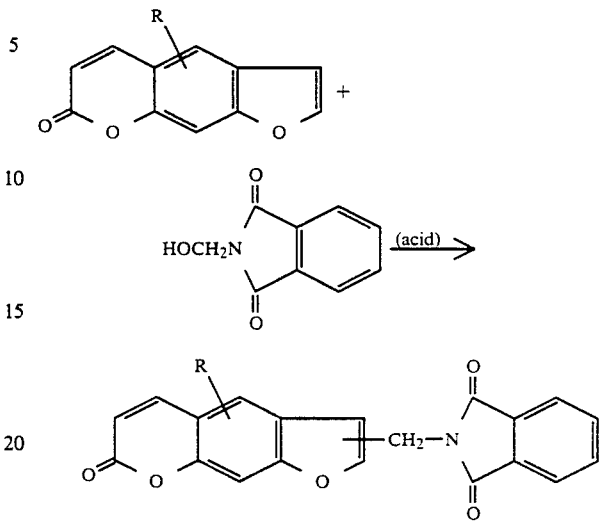

Polysubstitution of more than one methylphthalimido group onto the psoralen ring or acid-induced decomposition of the product can be avoided by operating at or below room temperature (10°–22° C.), carefully regulating the relative quantities of psoralen and N-hydroxymethylphthalimide (the latter in no more than 20–45% excess over the former), adding the equimolar quantity of the strong acid catalyst (concentration relative to the psoralen) to a vigorously agitated solution or suspension of the two condensing reagents, selecting suitable psoralens (as noted later herein) and employing anhydrous reaction conditions. While other aminomethylating agents such as N-hydroxymethylbenzamide, N-hydroxymethylacetamide, and N,N'-dimethyl-N-hydroxymethylurea might be employed, these undergo in situ self condensation, acid-induced decomposition, or polysubstitution on the psoralen ring. The steric bulk, resistance to self-condensation, and selectivity as to the site of psoralen-directed attack (4' or 5') which characterize the properties of N-hydroxymethylphthalimide make the latter the aminomethylating agent of choice. At concentration ratios of N-hydroxymethylphthalimide to psoralen of 1 to 1.5, the only examples of polycondensation and multi-site attack on the psoralen ring were observed with psoralens bearing hydroxy, methoxy, and amino substituents. Not only are psoralens with these functions susceptible to multi-substitution, but the phthalimido moieties cannot be readily cleaved by the process in Step II described below.

Psoralens bearing hydrogen, methyl, and lower alkyl as claimed herein generate isolable aminomethylphthalimides consisting of a single substitution product. Even when positions 3, 4, 5, and 8 are unsubstituted (i.e., bearing only a hydrogen), the entering N-phthalimidomethyl group is directed to the furano ring of the psoralen. If methyl or lower alkyl substitution is present at carbon 4' the process described herein places the methylphthalimide at carbon 5' and if methyl or lower alkyl substitution is present at carbon 5' this process directs the methylphthalimide to carbon 4'.

The acid should be added to the psoralen and the N-hydroxymethylphthalimide over 15–30 minutes and the entire reaction contents agitated vigorously at room temperature for 4 to 24 hours. In all cases the reactions were essentially complete at 6 hours and the additional time did not contribute appreciably to higher yields. Published procedures for implementation of the chloromethylation technique on psoralens—the process which is supplanted by the technique described herein—state that long contact times (40-72 hours) are needed to ensure high yield conversion [see U.S. Pat. Nos. 4,124,598 and 4,294,822; S. T. Isaacs et al., *Biochemistry*, 16, 1058 (1977); K. D. Kaufman et al., *J. Heterocyclic Chem.*, 19, 1051 (1982)]. Yields in Step I of the direct aminomethylation as described herein were 60-80% at the end of 6 hours of contact with average conversions of 70% being readily possible. Since Step I in this improved procedure replaces two distinct reaction steps in the earlier process (chloromethylation and phthalimide displacement), the saving in operating time as well as in overall conversion yields is appreciable.

Step II of the reaction is the liberation of the free aminomethylpsoralen by hydrazine cleavage of the N-phthalimidomethylpsoralen in hydrazine hydrate and ethanol for 4 to 24 hours.

STEP II

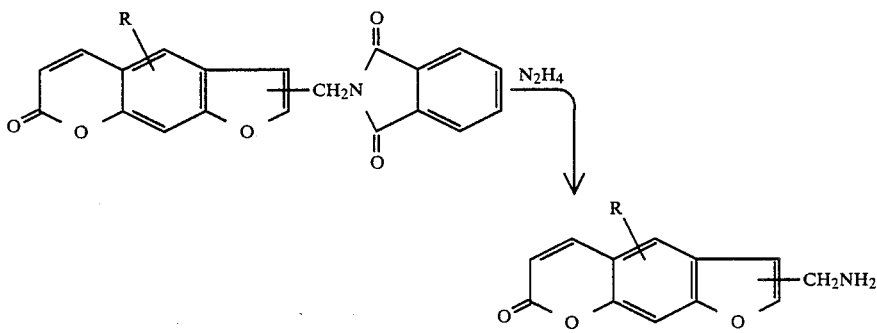

In most cases the reaction was complete after 6 hours and additional time did not contribute to higher yields. The aminomethylpsoralens could be isolated as their free base or hydrochloride forms. Yields of the free base aminomethylpsoralens were 60-70% with 65% conversions readily possible. Overall yields in the two steps of this reaction sequence are 40 to 55%. This represents 5 to 20% greater conversions than those reported in the three-step aminomethylations using the carcinogenic alpha-haloalkyl ethers (see, Isaacs et al., *Biochem.*, 16, 1058 (1977) and U.S. Pat. No. 4,294,822).

EXAMPLE #1

5'-AMINOMETHYL-4,4',8-TRIMETHYLPSORALEN

Step I:
5'-N-phthalimidomethyl-4,4',8-trimethylpsoralen

A suspension of 4,4',8-trimethylpsoralen (9.0 g, 0.039 moles) and N-hydroxymethylphthalimide (10.0 g, 0.056 moles) in 250 ml of anhydrous methylene chloride is stirred vigorously and treated to the dropwise addition of 6.0 g, 0.040 moles, of trifluoromethanesulfonic acid dissolved in 26 ml of trifluoroacetic acid. The addition was carried out over 15 to 30 minutes to hold the reaction temperature within 5° C. of room temperature without external cooling. The entire reaction mixture was then agitated at ambient temperature for 6 hours, evaporated to dryness in vacuo, and the dark purple solid exposed to vacuum over KOH pellets in a dessicator for 12 hours. This procedure is a convenient method to remove most of the excess acid catalyst and the trifluoroacetic acid solvent.

The dark-colored mass was triturated with approximately 500 ml of water and filtered to give a yellow-white solid. Sufficient chloroform was added to dissolve this solid at ambient temperatures and the chloroform solution washed with two portions of 250 ml each of water. The organic phase was dried over $MgSO_4$, the drying agent filtered off, the solvent evaporated to a volume of approximately 30 ml, and the medium chilled in ice. The precipitated product was isolated by filtration and a second crop was obtained by further concentration and chilling of the chloroform mother liquors. These crystal crops were recrystallized from chloroform to yield a light yellow solid, mp 273°-275°, 10 g or 70% yield. Thin layer chromatograms ($SiO_2$ plates) of this solid in chloroform ($R_f$=0.47) in ethyl acetate, ($R_f$=0.70) or in 4:9 ethyl acetate:benzene ($R_f$=0.77) showed a single spot.

Anal. Calcd. for $C_{23}H_{17}NO_5 \cdot \frac{1}{4}H_2O$: C, 70.48; H, 4.50; N, 3.57. Found: C, 70.15; H, 4.33; N, 3.35.

Step II; 5'-Aminomethyl-4,4',8-trimethylpsoralen

A mixture of 5'-N-phthalimidomethyl-4,4',8-trimethylpsoralen (8.0 g, 0.021 moles), hydrazine hydrate (26 ml) and 95% ethanol (800 ml) was heated at reflux for 6 hours and then concentrated in vacuo to a crude solid residue. This residue was taken up to form a turbid suspension in 0.1N NaOH, 1800 ml total volume, and extracted with chloroform several times (total $CHCl_3$=2000 ml). The extract was washed with water, dried over $MgSO_4$, and the chloroform removed in vacuo. An off-white solid, m.p. 204°-208° C. [lit m.p. 197°-199° C.; U.S. Pat. No. 4,294,822] 3.5 g, 65% yield, was obtained. The thin layer chromatogram ($SiO_2$ plates) in 5:0.5 chloroform-methanol showed a single spot ($R_f$=0.43).

Anal. Calcd. for $C_{15}H_{15}NO_3$: C, 70.02; H, 5.88; N, 5.44. Found: C, 69.77; H, 6.22; N, 5.21.

If the free base is dissolved in anhydrous diethyl ether filtered to remove a trace of suspended insolubles, and treated to the slow passage of anhydrous hydrogen chloride gas, a pink hydrochloride salt precipitates in >90% yield. This hydrochloride, m.p. 304°-307° C. is an extremely hygroscopic material, readily soluble in water, and recrystallizable from anhydrous methanol. Melting point values, however, must be obtained by permitting a rapid rise (ca. 3°-4° C. per minute) in the temperature in the melting apparatus. Psoralen aminomethyl hydrochlorides underwent slow decomposition to thermally refractory dark-colored solids when heated slowly under customary melting-point methods.

Rapid temperature rise did permit the observation of a definite solid-to-liquid transition, usually with concomitant decomposition.

Anal. Calcd. for $C_{15}H_{15}NO_3.HCl.\frac{3}{4}H_2O$: C, 58.68; H, 5.75; N, 4.56%. Found: C, 58.71; H, 5.46; N, 4.88%.

EXAMPLE #2

4'-AMINOMETHYL-4,5',8-TRIMETHYLPSORALEN

Step I:
4'-N-Phthalimidomethyl-4,5',8-trimethylpsoralen

Trifluoromethanesulfonic acid (3.0 g, 0.020 moles) and trifluoroacetic acid (25 ml) were added dropwise over 15 minutes to a well-stirred mixture of 4,5',8-trimethylpsoralen (trioxsalen) (4.50 g; 0.020 moles) [prepared as described in K. D. Kaufman and L. E. Hewitt, *J. Org. Chem.*, 45, 738 (1980)] and N-hydroxymethylphthalimide (5.00 g; 0.028 m) in dry methylene chloride (100 ml) at room temperature. Stirring was continued for 6 hrs. Evaporation in vacuo gave a greenish solid which could be freed of acid by evacuating over KOH pellets for 24 hours or by triturating with 5% aqueous sodium bicarbonate, followed by filtration. Following either method the solid was dissolved in chloroform. The chloroform extract was washed with water, dried ($MgSO_4$) and evaporated to approximately 25 ml to precipitate a yellow solid.

Recrystallization from chloroform gave a pale yellow solid, 5.0 g. (60% yield) m.p. 274°–276° [lit m.p. 267°–274°]. The product obtained by the single step route described above displayed spectra identity (infrared and NMR) to the substance obtained in the two-step process (S. T. Isaacs, et al., *Biochem.*, 16, 1058 (1977).

Step II: 4'-Aminomethyl-4,5',8-trimethylpsoralen

A mixture of 4'-N-phthalimidomethyl-4,5',8-trimethylpsoralen (1.0 g; 0.002 moles), hydrazine hydrate (85% in water, 4.0 ml) and ethanol (95%, 110 ml) was refluxed for 6 hrs. Evaporation to dryness gave a yellow solid residue which was suspended in 0.1N NaOH (250 ml) and extracted with chloroform (400 ml). The chloroform extract was washed with water and dried ($MgSO_4$). Evaporation of solvent gave the amine as an off-white solid (0.50 g 80% yield), m.p. 197°–199° C. This amine gave a single spot ($R_f$=0.22) in thin layer chromatographic analysis, silica plates, 5.0:0.5 $CHCl_3$:MeOH.

Anal. Calcd. for $C_{15}H_{15}NO_3$: C, 70.02; H, 5.87; N, 5.44. Found: C, 69.82; H, 5.75; N, 5.30.

If the free base is dissolved in anhydrous diethyl ether, filtered, and treated to the slow passage of anhydrous hydrogen chloride gas, a highly hygroscopic hydrochloride salt precipitates in 85% yield. After vacuum drying this salt melts at 320°–325° C. (with 3° C./minute elevation of block temperature). Slower heating rates demonstrate only a darkening and decomposition to a charred solid which does not melt below 330° C.

Anal. Calcd. for $C_{15}H_{15}NO_3.HCl.\frac{3}{4}H_2O$: C, 58.68; H, 5.75; N, 4.56. Found: C, 58.82; H, 5.98; N, 4.45.

Tetrahydrofuran is an alternative solvent (to diethyl ether) for precipitation of these aminomethyl hydrochlorides but it can be employed only for small-scale reactions (less than 5–10 g of free base amine). Larger amounts of amine require a longer passage time to deliver sufficient HCl gas into the solvent medium and to effect a quantitative precipitation of the hydrochloride. Tetrahydrofuran has been found to react slowly with the HCl gas and produce byproduct contaminants if the precipitation of the salt is not completed in less than 10 minutes.

EXAMPLE #3

5'-AMINOMETHYL-4,4'-DIMETHYLPSORALEN

Step I: 5'-N-Phthalimidomethyl-4,4'-dimethylpsoralen

A solution of trifluoromethanesulfonic acid (0.75 g., 5.0 mmoles) in 10 ml. trifluoroacetic acid was added slowly to a well-stirred mixture of 4,4'-dimethylpsoralen (1.07 g., 5.0 mmoles) and N-hydroxymethylphthalimide (1.24 g., 7.0 mmoles) in 150 ml. of anhydrous methylene chloride. The slow addition of reagents was carried out at room temperature without external cooling. The contents of the reaction mixture were stirred at room temperature for 12 hours.

The solvent was then removed from the reaction mixture in vacuo leaving a dark, red-purple residue. This residue was exposed to high vacuum for 5 hours to remove residual solvent and acidic catalysts. The dark solid was then dissolved in chloroform (500 ml.) and washed with cold water (3×200 ml.). The color of the chloroform solution changed to yellow during the washing procedure. The chloroform solution was dried over $MgSO_4$, filtered, and evaporated in vacuo to yield an off-white residue which was recrystallized from chloroform to yield straw colored crystals of the title compound m.p. 297°–299° C., 1.14 g (61% yield). Anhydrous phthalimide can be obtained by sublimation in vacuo and melts at 316°–318° C. [see, K. D. Kaufman et al., *J. Heterocyclic Chem*, 19, 1051 (1982)].

Anal. Calcd. for $C_{22}H_{15}NO_5.\frac{3}{4}H_2O$: C, 68.31; H, 4.28; N, 3.62. Found: C, 68.00; H, 3.74; N, 3.82.

Step II: 5'-Aminomethyl-4,4'-dimethylpsoralen

A mixture of 5'-N-phthalimidomethyl-4,4'-dimethylpsoralen (0.965 g. 2.58 mmole), hydrazine hydrate, 85% (4 ml) and 95% ethanol (100 ml) was heated to reflux for 12 hours. Solvent was then removed in vacuo to yield a solid residue. This residue was slurried in 0.1N NaOH (400 ml) and extracted with chloroform several times (total chloroform=300 ml). The extract was washed with water, dried over $MgSO_4$, and reduced in volume to yield an off-white solid, 0.373 g., 59% yield m.p. 182°–185° C. (lit m.p. 186°–188° C., see K. Kaufman et al., *J. Heterocyclic Chem.*, 19, 1051 (1982).

Anal. Calcd. for $C_{14}H_{13}NO_3.\frac{1}{4}H_2O$: C, 67.47; H, 5.52; N, 5.62. Found: C, 67.35; H, 5.66; N, 5.55.

A thin-layer chromatograph in 5.0:0.5 $CHCl_3$:MeOH on silica gel plates gave a single spot with an $R_f$ of 0.44. The hygroscopic hydrochloride salt formed by the previously described method had a decomposition point of 308°–312° C.

Anal. Calcd. for $C_{14}H_{13}NO_3.HCl$: C, 60.11; H, 5.05; N, 5.01. Found: C, 59.75; H, 5.40; N, 4.80.

EXAMPLE #4

5'-AMINOMETHYL-4'-METHYLPSORALEN

Step I: 5'-N-Phthalimidomethyl-4'-methylpsoralen

A suspension prepared from (4.00 g, 0.020 moles) of 4'-methylpsoralen and 4.40 g, 0.025 moles of N-hydroxymethylphthalimide in 120 ml of anhydrous methylene chloride was stirred vigorously at room temperature while a solution of trifluoromethanesulfonic acid (3.0 g, 0.020 moles) in 30 ml of trifluoracetic acid was added dropwise. The addition was carried out over 30 minutes with temperature monitoring and occasional cooling in an ice-water bath to maintain the temperature below 25° C. After completion of the addition, the contents were stirred at room temperature for 10 hours, the solvent was removed by evaporation in vacuo, and the dark semi-solid residue triturated with 5% aqueous sodium bicarbonate to neutralize the acidic components. The crude product was then dissolved in 500 ml of chloroform, this organic phase washed with 3×150 ml portions of water, and then dried over MgSO$_4$. Evaporation of the filtered chloroform solution gave an ivory-colored solid (5.39 g, 74% yield) which was recrystallized from 9:1 acetic acid:water to generate the analytical sample, mp 268°–270° C. [lit. m.p. 270.0°–270.5° C., see K. D. Kaufmanm, et al., *J. Heterocyclic Chem.*, 19, 1051 (1982)].

Anal. Calcd. for $C_{21}H_{13}NO_5$: C, 70.19; H, 3.62; N, 3.90. Found: C, 69.78; H, 3.99; N, 3.60.

Step II: 5′-Aminomethyl-4′-methylpsoralen

A mixture of 5′-N-phthalimidomethyl-4′-methylpsoralen (4.00 g, 11.1 mmoles) 22 ml of 85% hydrazine hydrate and 500 ml of 95% ethanol was stirred at reflux for 10 hours. The mixture was then concentrated in vacuo to a crude dark-colored solid which formed a turbid suspension in 1 L. of 0.1N NaOH. This aqueous phase was extracted with 4×200 ml portions of methylene chloride and the extracts dried over MgSO$_4$. Filtration of the methylene chloride solution and evaporation in vacuo gave 2.01 g, 79% yield, of an off-white solid, mp 152°–154° C., (lit. mp 153°–156° C., see, K. D. Kaufman, et al., *J. Heterocyclic Chem.*, 19, 1051 (1982).

Anal. Calcd. for $C_{13}H_{11}NO_3$: C, 68.12; H, 4.84; N, 6.11. Found: C, 67.79; H, 5.05; N, 5.88.

OTHER EXAMPLES

Other psoralens to which the herein described two-step aminomethylation can be applied and for which conversions to aminomethyl derivatives can be obtained in 40–55% yield range, are 4,5′-dimethyl-8-n-propylpsoralen, 4′,8-dimethyl-4-m-propylpsoralen, 4,5′-dimethylpsoralen, 8-chloro-4,5′-dimethylpsoralen, 4-methyl-8-n-propylpsoralen and any other appropriately substituted psoralen fitting the substitution pattern described previously herein.

Thus, an improved process is disclosed for introducing the aminomethyl moeity into psoralens. While applications and examples of this invention have been shown and described, it would be apparent to those skilled in the art that many more modifications are possible without departing from the invention. The invention therefore, is not to be restricted except in the spirit of the appended claims.

We claim:

1. A process for introducing the aminomethyl moiety (CH$_2$NH$_2$) onto the furan ring of a psoralen or furocoumarin ring structure, said psoralen or furocoumarin ring structure being unsubstituted or substituted with a lower alkyl group at the C-4 position, said process consisting of:
   (1) reacting under anhydrous conditions, a mixture of a psoralen or furocoumarin and an aminomethylating agent selected from the group consisting of N-hydroxymethylphthalimide, N-hydroxymethylbenzamide, N-hydroxymethylacetamide, and N-N′-dimethyl-N-hydroxymethylurea suspended or dissolved in an anhydrous polar solvent with a strong protonic acid, Lewis acid or mixture of such acids, and
   (2) separating the aminomethylated psoralen or furocoumarin by hydrazine cleavage in hydrazine hydrate and ethanol to produce a 4′ or 5′ aminomethyl psoralen or furocoumarin.

2. The process of claim 1 wherein said lower alkyl substituted psoralen is selected from the group consisting of 4,5′,8-trimethylpsoralen; 4,4′,8-trimethylpsoralen; 4′,8-dimethyl-8-ethylpsoralen; 4′-ethyl-4,8-dimethylpsoralen; 5′,8-dimethylpsoralen; 4,5′-dimethyl-8-n-propylpsoralen, 4′,8-dimethyl-4-m-psopylpsoralen, 4,5′-dimethylpsoralen; and 4-methyl-8-n-propylpsoralen.

3. The process of claim 1 wherein said anhydrous polar solvent is selected from the group consisting of chloroform, methylene chloride, acetic acid and formic acid.

4. The process of claim 1 wherein said protonic or Lewis acid is selected from the group consisting of trifluoroacetic acid, methane sulfonic acid, trifluoromethane sulfonic acid, boron trifluoride etherate and fuming sulfuric acid.

5. The process of claim 1 wherein Step (1) of the reaction sequence is carried out in the temperature range of about 10°–22° C.

6. The process of claim 1 wherein the relative quantity of said aminomethylating agent is no more than about 20–45% greater than said psoralen.

7. A process for introducing the aminomethyl moiety (—CH$_2$NH$_2$) onto psoralen which consist of:
   (1) reacting, under anhydrous conditions, a mixture of 4,4′,8-trimethylpsoralen and N-hydroxymethylphthalimide suspended in methylene chloride treated to dropwise addition of trifluoromethanesulfonic acid dissolved in trifluoroacetic acid, and
   (2) cleaving the resulting 5′-N-phthalimidomethyl-4,4′,8-trimethylpsoralen in hydrazine hydrate and 95% ethanol to yield 5′-aminomethyl-4,4′,8-trimethylpsoralen.

8. A process for introducing the aminomethyl moiety (—CH$_2$NH$_2$) onto psoralen which consist of:
   (1) reacting, under anhydrous conditions, a mixture of 4,5′,8-trimethylpsoralen and N-hydroxymethylphthalimide suspended in methylene chloride treated to dropwise addition of trifluoromethane sulfonic acid and trifluoroacetic acid, and
   (2) cleaving the resulting 4′-N-phthalimidomethyl-4,5′,8-trimethylpsoralen in hydrazine hydrate and 95% ethanol to yield 4′-aminomethyl-4,5′,8-trimethylpsoralen.

9. A process for introducing the aminomethyl moiety (—CH$_2$NH$_2$) onto psoralen which consist of:
   (1) reacting, under anhydrous conditions, a mixture of 4,4′-dimethylpsoralen and N-hydroxymethylphthalimide suspended in methylene chloride treated to dropwise addition of trifluoromethanesulfonic acid and trifluoroacetic acid, and
   (2) cleaving the resulting 5′-N-phthalimidomethyl-4,4′-dimethylpsoralen in hydrazine hydrate and 95% ethanol to yield 5′-aminomethyl-4,4′-dimethylpsoralen.

10. A process for introducing the aminomethyl moiety (—CH$_2$NH$_2$) onto psoralen which consist of:
   (1) reacting, under anhydrous conditions, a mixture of 4′-methylpsoralen and N-hydroxymethylphthalimide suspended in methylene chloride treated to dropwise addition of trifluoromethanesulfonic acid and trifluoroacetic acid, and
   (2) cleaving the resulting 5′-N-phthalimidomethyl-4′-methylpsoralen in hydrazine hydrate and 95% ethanol to yield 5′-aminomethyl-4′-methylpsoralen.

* * * * *